United States Patent [19]

Holmwood et al.

[11] Patent Number: 4,515,617

[45] Date of Patent: May 7, 1985

[54] BENZYL-PYRIMIDINYLALKYL-ETHERS AS PLANT GROWTH REGULATORS AND FUNGICIDES, AND CORRESPONDING PYRIMIDINYLCARBINOLS

[75] Inventors: Graham Holmwood, Wuppertal; Klaus Lürssen, Berg.-Gladbach; Paul-Ernst Frohberger, Leverkusen, all of Fed. Rep. of Germany

[73] Assignee: Bayer Aktiengesellschaft, Leverkusen, Fed. Rep. of Germany

[21] Appl. No.: 519,609

[22] Filed: Aug. 2, 1983

Related U.S. Application Data

[62] Division of Ser. No. 344,261, Jan. 28, 1982, Pat. No. 4,436,907.

[30] Foreign Application Priority Data

Feb. 14, 1981 [DE] Fed. Rep. of Germany ....... 3105374

[51] Int. Cl.³ ............................................. A01N 43/54
[52] U.S. Cl. ........................................ 71/76; 71/92; 514/256
[58] Field of Search ................... 71/76, 92; 424/251

[56] References Cited

U.S. PATENT DOCUMENTS

| 3,868,244 | 2/1975 | Taylor et al. | 71/76 |
| 3,967,949 | 7/1976 | Benefiel et al. | 71/76 |
| 4,118,217 | 10/1978 | Oestreicher et al. | 71/76 |
| 4,417,050 | 11/1983 | Cherpeck | 71/92 |
| 4,436,907 | 3/1984 | Holmwood et al. | 544/335 |

FOREIGN PATENT DOCUMENTS 1361816 7/1974 United Kingdom ................... 71/76

OTHER PUBLICATIONS

Holmwood et al., "Benzyl Pyrimidinylalkyl, etc.," (1982), CA 97, No. 216,216a, (1982).

Primary Examiner—Glennon H. Hollrah
Assistant Examiner—R. Lelkes
Attorney, Agent, or Firm—Sprung, Horn, Kramer & Woods

[57] ABSTRACT

A benzyl-pyrimidinylalkyl-ether of the formula

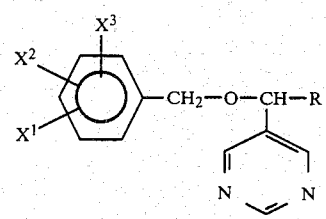

in which

R is alkyl, optionally substituted cycloalkyl or optionally substituted phenyl, and $X^1$, $X^2$ and $X^3$ each independently is hydrogen, halogen, alkyl, cycloalkyl, alkoxy, alkylthio, halogenoalkyl, halogenoalkoxy, halogenoalkylthio, cyano, optionally substituted phenoxy, optionally substituted phenylalkyl or optionally substituted phenylalkoxy, or an acid addition salt or metal salt complex thereof, which possesses fungicidal and plant growth-regulating properties. The corresponding pyrimidinyl-carbinols are also new.

5 Claims, No Drawings

BENZYL-PYRIMIDINYLALKYL-ETHERS AS PLANT GROWTH REGULATORS AND FUNGICIDES, AND CORRESPONDING PYRIMIDINYLCARBINOLS

This is a division of application Ser. No. 344,261, filed Jan. 28, 1982, now U.S. Pat. No. 4,436,907, issued Mar. 13, 1984.

The present invention relates to certain new benzyl-pyrimidinylalkyl-ethers, to a process for their preparation and to their use as plant growth regulators and fungicides. The invention also relates to certain new pyrimidinylcarbinols which are used as intermediate products for the preparation of benzyl-pyrimidinylalkyl-ethers, and to a process for the preparation of the pyrimidinylcarbinols.

It has already been disclosed that hydroxypyrimidine derivatives, for example 2-chlorophenyl-4-fluorophenyl-pyrimidin-5-yl-methanol or 4-fluorophenyl-phenyl-pyrimidin-5-yl-methanol, have good pesticidal properties (see U.S. Pat. Nos. 3,818,009, 3,868,244, 3,869,456 and 3,887,708).

It has already been disclosed, in addition, that 3-substituted pyridine derivatives, for example 1-(2,4-dichlorophenoxy)-2-phenyl-1-pyridin-3-yl-2-ethanone or 1-(4-chloro-2-methylphenoxy)-2-phenyl-1-pyridin-3-yl-ethanone, have good fungicidal properties (see DE-OS (German Published Specification) No. 2,909,287). However, the action of all these compounds, particularly when small quantities and low concentrations are used, is not always completely satisfactory.

The present invention now provides, as new compounds, the benzyl-pyrimidinylalkyl-ethers of the general formula

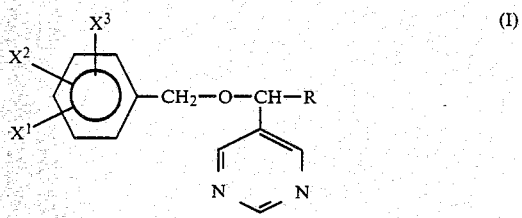

in which
R represents alkyl, optionally substituted cycloalkyl or optionally substituted phenyl and
$X^1$, $X^2$ and $X^3$ are selected independently and each represent hydrogen, halogen, alkyl, cycloalkyl, alkoxy, alkylthio, halogenoalkyl, halogenoalkoxy, halogenoalkylthio, cyano, optionally substituted phenyl, optionally substituted phenoxy, optionally substituted phenylalkyl or optionally substituted phenylalkoxy,
and the acid-addition salts and metal-salt complexes thereof.

The compounds of the formula (I) have an asymmetric carbon atom; they can therefore occur as the two optical isomers or as the racemate. All of the isomers are comprehended by formula (I)

The present invention also provides a process for the preparation of a benzyl-pyrimidinylalkyl-ether of the formula (I), or an acid addition salt or metal salt complex thereof, in which a pyrimidinyl-carbinol of the general formula

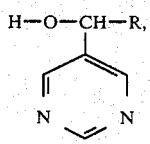

in which R has the meaning given above, is reacted with a benzyl halide of the general formula

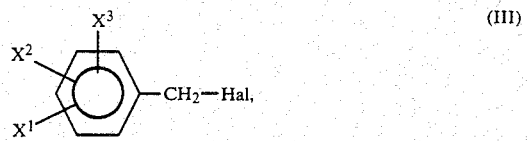

in which
$X^1$, $X^2$ and $X^3$ have the meanings given above and
Hal represents halogen, in the presence of a solvent and, if appropriate, in the presence of a strong base or, if appropriate, in the presence of an acid-binding agent, and, if required, an acid or a metal salt is added onto the resultant compound.

It has been found that the benzyl-pyrimidinyl-alkyl-ethers of the formula (I) and the acid addition salts and metal salt complexes thereof have powerful plant growth-regulating and fungicidal properties.

Surprisingly, the compounds of the formula (I) according to the invention show a better growth-regulating action than the known hydroxypyrimidine derivatives from the state of the art, and a better fungicidal action than the 3-substituted pyridine derivatives which are likewise known. The active compounds according to the invention thus represent an enrichment of the art.

Formula (I) gives a general definition of the benzyl-pyrimidinylalkyl-ethers according to the invention. Preferably, in this formula, R represents straight-chain or branched alkyl having 1 to 8 carbon atoms; cycloalkyl which has 3 to 7 carbon atoms and which is optionally substituted by alkyl having 1 to 4 carbon atoms; or optionally substituted phenyl, preferred substituents being halogen, alkyl and alkoxy, each having 1 to 4 carbon atoms, and halogenoalkyl having 1 to 2 carbon atoms and 1 to 5 identical or different halogen atoms (especially fluorine atoms and chlorine atoms), $X^1$ represents hydrogen, halogen, straight-chain or branched alkyl having 1 to 4 carbon atoms, cycloalkyl having 3 to 7 carbon atoms, alkoxy or alkylthio, each having 1 to 4 carbon atoms, halogenoalkyl, halogenoalkoxy or halogenoalkylthio, each having 1 to 4 carbon atoms and 1 to 5 identical or different halogen atoms (especially fluorine atoms and chlorine atoms), cyano or optionally substituted phenyl, phenoxy, phenylalkyl having 1 to 4 carbon atoms in the alkyl part or phenylalkoxy having 1 to 4 carbon atoms in the alkoxy part, preferred substituents in each case being halogen and/or alkyl having 1 to 4 carbon atoms, $X^2$ represents hydrogen, halogen, straight-chain or branched alkyl having 1 to 4 carbon atoms, cycloalkyl having 3 to 7 carbon atoms, alkoxy or alkylthio, each having 1 to 4 carbon atoms, or halogenoalkyl, halogenoalkoxy or halogenoalkylthio, each having 1 to 4 carbon atoms and 1 to 5 identical or different halogen atoms (especially fluorine atoms and chlorine atoms), and $X^3$ represents hydrogen, halogen, straight-chain or branched alkyl having 1 to 4 carbon atoms, cycloalkyl having 3 to 7 carbon atoms, alkoxy or alkylthio, each having 1 to 4 carbon atoms, or halogenoalkyl, halogenoalkoxy or halogenoalkylthio, each having 1 to 4 carbon atoms and 1 to 5 identical or different halogen atoms (especially fluorine atoms and chlorine atoms).

Particularly preferred compounds of the formula (I) are those in which

R represents isopropyl, isobutyl, tert.-butyl, n-pentyl, n-hexyl, optionally methyl-substituted cyclopentyl or cyclohexyl, or phenyl which is optionally substituted by fluorine, chlorine, methyl, methoxy or trifluoromethyl, $X^1$ represents hydrogen, fluorine, chlorine, methyl, tert.-butyl, cyclohexyl, methoxy, methylthio, trifluoromethyl, trifluoromethoxy, trifluoromethylthio, cyano, or phenyl, phenoxy, benzyl or benzyloxy, each of which is optionally substituted by fluorine, chlorine or methyl, $X^2$ represents hydrogen, fluorine, chlorine, methyl, tert.-butyl, cyclohexyl, methoxy, methylthio, trifluoromethyl, trifluoromethoxy or trifluoromethylthio, and $X^3$ represents hydrogen, fluorine, chlorine, methyl, methoxy, methyl or trifluoromethyl.

In addition to the compounds mentioned later in the preparative examples, the following compounds of the general formula (I) may be individually mentioned:

TABLE 1

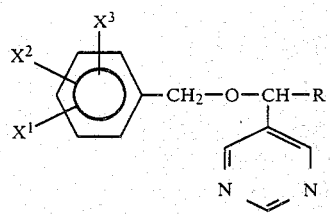

(I)

| $X^1$ | $X^2$ | $X^3$ | R |
|---|---|---|---|
| 4-Cl | H | H | 4-Cl-C6H4 |
| 4-F | H | H | 4-Cl-C6H4 |
| 4-Cl | 2-Cl | H | 4-Cl-C6H4 |
| 2-Cl | 6-F | H | 4-Cl-C6H4 |
| 4-C6H5 | H | H | 4-Cl-C6H4 |
| 4-CF3 | H | H | 4-Cl-C6H4 |
| 3-Cl | 4-Cl | H | 4-Cl-C6H4 |
| 4-OCH3 | H | H | 4-Cl-C6H4 |
| 4-OCF3 | H | H | 4-Cl-C6H4 |
| 4-Cl | H | H | —(CH2)5—CH3 |
| 4-F | H | H | —(CH2)5—CH3 |
| 2-Cl | 4-Cl | H | —(CH2)5—CH3 |
| 2-Cl | 6-F | H | —(CH2)5—CH3 |
| 4-C6H5 | H | H | —(CH2)5—CH3 |
| 4-CF3 | H | H | —(CH2)5—CH3 |
| 3-Cl | H—Cl | H | —(CH2)5—CH3 |
| 4-OCH3 | H | H | —(CH2)5—CH3 |
| 4-OCF3 | H | H | —(CH2)5—CH3 |
| 4-Cl-C6H4 | H | H | —C(CH3)3 |
| 4-Cl-C6H4-O— | H | H | —C(CH3)3 |
| 4-Cl-C6H4-O— | H | H | —C(CH3)3 |
| C6H5-CH2— | H | H | —C(CH3)3 |

TABLE 1-continued

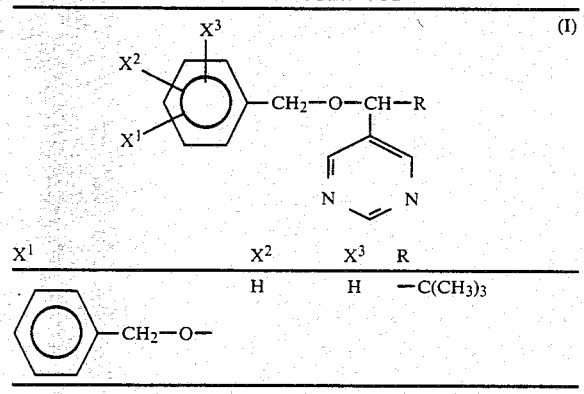

| X¹ | X² | X³ | R |
|---|---|---|---|
| H | H |  | —C(CH$_3$)$_3$ |

If, for example 2,2-dimethyl-1-hydroxy-1-(pyrimidin-5-yl)-propane and 4-chlorobenzyl chloride are used as starting materials and sodium hydride is used as the base, the course of the reaction can be represented by the following equation:

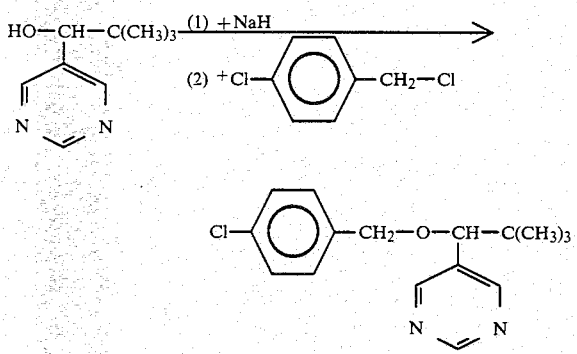

Formula (II) gives a general definition of the pyrimidinyl-carbinols to be used as starting materials in carrying out the process according to the invention. In this formula, R preferably represents those radicals which have already been mentioned in connection with the description of the compounds of the formula (I) as being preferred.

The pyrimidinyl-carbinols of the formula (II) have not hitherto been described in the literature. However, they can be obtained in a known manner by a process in which pyrimidine halides of the general formula

in which Z represents halogen, particularly chlorine or bromine,
are reacted with aldehydes of the general formula $$O=C-R \qquad (V),$$

in which R has the meaning given above,
in the presence of a diluent and in the presence of an alkali metal-organic compound.

Inert organic solvents are preferred diluents for the preparation of the pyrimidinyl-carbinols of the formula (II). These include, as preferences, those solvents which have a low melting point, such as ethers, for instance diethyl ether or tetrahydrofuran. The reaction is preferably carried out using mixtures of these two ethers.

The preparation of the compounds of the formula (II) is effected in the presence of an alkali metal-organic compound. Alkali metal-alkyls, such as n-butyl-lithium, are preferably employed for this purpose; alkali metal-aryls, such as phenyl-lithium, can also be used.

In carrying out this process, the reaction temperatures can be varied within a particular range. In general the reaction is carried out at temperatures between −150° C. and −50° C., preferably between −120° C. and −80° C.

This process is preferably carried out under an inert gas, such as, in particular, nitrogen or argon.

In carrying out this process, 1 to 2 moles of aldehyde of the formula (V) are preferably employed per mole of pyrimidine halide of the formula (IV). The alkali metal-organic compound is advantageously used in an excess of 5 to 75 mole percent, preferably of 10 to 50 mole percent The isolation of the compounds of the formula (II) is effected by hydrolyzing, for example with saturated ammonium chloride solution or with water, the alkali metal alkanolate (for example lithium-alkanolate) which is first formed in the reaction. The further working-up is then effected in the customary manner.

The pyrimidinyl-carbinols of the formula (II) represent generally interesting intermediate products, for example for the preparation of the compounds of the formula (I).

The pyrimidine halides of the formula (IV) and the aldehydes of the formula (V) are generally known compounds of organic chemistry.

Formula (III) provides a general definition of the benzyl halides additionally to be used as starting materials in carrying out the process according to the invention. In this formula, $X^1$, $X^2$ and $X^3$ preferably represent those radicals which have already been mentioned in connection with the description of the compounds of the formula (I) as being preferred. Hal preferably represents chlorine or bromine.

The benzyl halides of the formula (III) are generally known compounds of organic chemistry.

Inert organic solvents are preferred solvents for the process according to the invention. These include as preferences, ethers, such as diethyl ether or dioxane; aromatic hydrocarbons, such as toluene and benzene; and dimethylsulphoxide or dimethylformamide.

In carrying out the process according to the invention, the reaction temperatures can be varied within a wide range. In general, the reaction is carried out at a temperature between 0° and 100° C., preferably between 20° and 80° C.

The process according to the invention can be carried out, if appropriate, in the presence of a strong base. These include, as preferences, alkali metal hydrides, alkali metal amides and alkali metal alcoholates, for example sodium hydride, sodium amide and potassium tert.-butylate.

The process according to the invention can be carried out, if appropriate, in the presence of acid-binding agents. These include organic bases, preferably tertiary amines, and inorganic bases, for example alkali metal hydroxides.

In carrying out the process according to the invention, 1 to 3 moles of benzyl halide of the formula (III)

are preferably employed per mole of compound of the formula (II). The isolation of the end products of the formula (I) is effected in the customary manner.

In preferred embodiments, the process is advantageously carried out in such a manner that the pyrimidinylcarbinol of the formula (II), in a suitable inert organic solvent, is converted by means of an alkali metal hydride or alkali metal amide into the alkanolate, and the latter is immediately reacted, without isolation, with a benzyl halide of the formula (III), the compounds of the formula (I) according to the invention being obtained in one operation, with elimination of alkali halide.

According to further preferred embodiments, the reaction according to the invention is carried out in a two-phase system, such as, for example, aqueous sodium hydroxide or potassium hydroxide solution/toluene or methylene chloride, with the addition of 0.01–1 mole of a phase transfer catalyst, for example an ammonium compound or phosphonium compound, tetrabutylammonium bromide, benzyl-dodecyl-dimethyl-ammonium chloride (Zephirol) and triethylbenzyl-ammonium chloride being mentioned as examples.

The following are preferred acids which are suitable for the preparation of acid addition salts of the compounds of the formula (I); the hydrohalic acids (for example hydrobromic acid and, particularly, hydrochloric acid), phosphoric acid, nitric acid, sulphuric acid, monofunctional and bifunctional carboxylic acids and hydroxycarboxylic acids (for example acetic acid, maleic acid, succinic acid, fumaric acid, tartaric acid, citric acid, salicylic acid, sorbic acid and lactic acid) and sulphonic acids (for example p-toluenesulphonic acid and 1,5-naphthalenedisulphonic acid).

The acid addition salts of the compounds of the formula (I) can be obtained in a simple manner by customary methods of salt formation, for example by dissolving a compound of the formula (I) in a suitable inert solvent and adding the acid, for example hydrochloric acid, and can be isolated in a known manner, for example by filtering off, and can be purified, if appropriate, by washing with an inert organic solvent.

Salts of metals of main groups II to IV and subgroups I and II and IV to VIII are preferred salts suitable for the preparation of metal salt complexes of the compounds of the formula (I), copper, zinc, manganese, magnesium, tin, iron and nickel being mentioned as examples.

Anions which are preferably derived from the following acids are suitable anions of the salts: hydrohalic acids (for example hydrochloric acid and hydrobromic acid), phosphoric acid and sulphuric acid.

The metal complexes of compounds of the formula (I) can be obtained in a simple manner by customary processes, for example by dissolving the metal salt in alcohol, for example ethanol, and adding the solution to the compound of the formula (I). Metal salt complexes can be isolated in a known manner, for example by filtering off, and can be purified, if appropriate, by recrystallization.

The active compounds which can be used according to the invention engage in the metabolism of the plants and can therefore be employed as growth regulators.

Experience to date of the mode of action of plant growth regulators has shown that an active compound can also exert several different actions on plants. The actions of the compounds depend essentially on the point in time at which they are used, relative to the stage of development of the plants, and on the amounts of active compound applied to the plants or their environment and the way in which the compounds are applied. In every case, growth regulators are intended to influence the crop plants in the particular manner desired.

Plant growth regulating compounds can be employed, for example, to inhibit vegetative growth of the plants. Such inhibition of growth is inter alia of economic interest in the case of grasses, since it is thereby possible to reduce the frequency of cutting the grass in ornamental gardens, parks and athletic fields, at borders, at airports or in fruit orchards. The inhibition of growth of herbaceous and woody plants at borders and in the vicinity of pipelines or overland lines or, quite generally, in areas in which heavy additional growth of plants is undesired, is also of importance.

The use of growth regulators to inhibit the growth in height of cereals is also important. The danger of lodging of the plants before harvesting is thereby reduced or completely eliminated. Furthermore, growth regulators can strengthen the stems of cereals, which again counteracts lodging. The use of growth regulators for shortening and strengthening the stem enables higher amounts of fertilizer to be applied to increase the yield, without danger of the cereal lodging.

In the case of many crop plants, inhibition of the vegetative growth makes denser planting possible, so that greater yields per area of ground can be achieved. An advantage of the smaller plants thus produced is also that the crop can be worked and harvested more easily.

Inhibition of the vegetative growth of plants can also lead to increases in yield, since the nutrients and assimilates benefit blossoming and fruit formation to a greater extent than they benefit the vegetative parts of plants.

Promotion of vegetative growth can also frequently be achieved with growth regulators. This is of great utility if it is the vegetative parts of the plants which are harvested. Promoting the vegetative growth can, however, also simultaneously lead to a promotion of generative growth, since more assimilates are formed, so that more fruit, or larger fruit, is obtained.

Increase in yield can in some cases be achieved by affecting the plant metabolism, without noticeable changes in vegetative growth. A change in the composition of plants, which in turn can lead to a better quality of the harvested products, can furthermore be achieved with growth regulators. Thus it is possible, for example, to increase the content of sugar in sugar beet, sugar cane, pineapples and citrus fruit or to increase the protein content in soya or cereals. Using growth regulators it is also possible, for example, to inhibit the degradation of desired constituents, such as, for example, sugar in sugar beet or sugar cane, before or after harvesting. It is also possible favorably to influence the production or the efflux of secondary plant constituents. The stimulation of the latex flux in rubber trees may be mentioned as an example.

Parthenocarpous fruit can be formed under the influence of growth regulators. Furthermore, the gender of the flowers can be influenced. Sterility of the pollen can also be produced, which is of great importance in the breeding and preparation of hybrid seed.

Branching of plants can be controlled by using growth regulators. On the one hand, by breaking the apical dominance the development of side shoots can be promoted, which can be very desirable, especially in the cultivation of ornamental plants, also in connection with growth inhibition. On the other hand, however, it is also possible to inhibit the growth of side shoots. There is great interest in this action, for example, in the cultivation of tobacco or in the planting of tomatoes.

The amount of leaf on plants can be controlled, under the influence of growth regulators, so that defoliation of the plants at a desired point in time is achieved. Such defoliation is of great importance in the mechanical harvesting of cotton, but is also of interest for facilitating harvesting in other crops, such as, for example, in viticulture. Defoliation of the plants can also be carried out to lower the transpiration of plants before they are transplanted.

The shedding of fruit can also be controlled with growth regulators. On the one hand, it is possible to prevent premature shedding of fruit. However, on the other hand, shedding of fruit, or even the fall of blossom, can be promoted up to a certain degree (thinning out) in order to interrupt the alternance. By alternance there is understood the peculiarity of some varieties of fruit to produce very different yields from year to year, for endogenic reasons. Finally, using growth regulators it is possible to reduce the force required to detach the fruit at harvest time so as to permit mechanical harvesting of facilitate manual harvesting.

Using growth regulators, it is furthermore possible to achieve an acceleration or retardation of ripening of the harvest product, before or after harvesting. This is of particular advantage, since it is thereby possible to achieve optimum adaptation to market requirements. Furthermore, growth regulators can at times improve the coloration of fruit. In addition, concentrating the ripening within a certain period of time is also achievable with the aid of growth regulators. This provides the preconditions for being able to carry out complete mechanical or manual harvesting in only a single pass, for example in the case of tobacco, tomatoes or coffee.

Using growth regulators, it is furthermore possible to influence the latent period of seeds or buds of plants, so that the plants, such as, for example, pineapple or ornamental plants in nurseries, germinate, shoot or blossom at a time at which they normally show no readiness to do so. Retarding the shooting of buds or the germination of seeds with the aid of growth regulators can be desirable in regions where frost is a hazard, in order to avoid damage by late frosts.

Finally, the resistance of plants of frost, drought or a high salt content in the soil can be induced with growth regulators. Cultivation of plants in regions which are usually unsuitable for this purpose thereby becomes possible.

The preferred time of application of the growth regulators depends on the climatic and vegetative circumstances.

The foregoing description should not be taken as implying that each of the compounds can exhibit all of the described effects on plants. The effect exhibited by a compound in any particular set of circumstances must be determined empirically.

The active compounds according to the invention also exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration by plants of the active compounds at the concentrations required for combating plant diseases, permits treatment of above-ground parts of plants, of vegetative propagation stock and seeds, and of the soil.

As plant protection agents, the active compounds according to the invention can be used with particularly good success for combating those fungi which cause powdery mildew diseases; thus, they can be used for combating Erysiphe species, for example against the powdery mildew of barley or powdery mildew of cereals causative organism (*Erysiphe graminis*) and the powdery mildew of cucumber causative organism (*Erysiphe cichoreacearum*).

In addition, the compounds according to the invention exhibit a broad fungicidal in vitro spectrum.

When used in appropriate concentrations, the substances according to the invention also exhibit a herbicidal action.

The active compounds can be converted into the customary formulations, such as solutions, emulsions, suspensions, powders, foams, pastes, granules, aerosols, very fine capsules in polymeric substances and in coating compositions for seed, as well as ULV formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl napthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters; polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methyl-cellulose.

Adhesives such as carboxymethylcellulose and natural and synthetic polymers in the form of powders, granules or latices, such as gum arabic polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in the formulations as a mixture with other active compounds, such as fungicides, insecticides, acaricides and herbicides, and also as mixtures with fertilizers and other growth regulators.

The active compounds can be used a such, in the form of their formulations or as the use forms prepared therefrom, such as ready-to-use solutions, emulsifiable concentrates, emulsions, foams, suspensions, wettable powders, pastes, soluble powders, dusting agents and granules. They may be used in the customary manner, for example by watering, spraying, atomising, scattering, dusting, foaming, coating and the like. Furthermore, it is possible to apply the active compounds in accordance with the ultra-low volume process or to inject the active compound preparation or the active compound itself into the soil. It is also possible to treat the seeds of plants.

When the compounds according to the invention are employed as plant growth regulators, the use quantities can be varied within a relatively wide range. In general 0.01 to 50 kg, preferably 0.05 to 10 kg, are used per hectare of soil area.

According to the type of application, the use quantity can be varied within a relatively wide range also when the substances according to the invention are employed as fungicides. Thus, especially in the treatment of parts of plants, the active compound concentrations in the use forms are, in general, between 1 and 0.0001% by weight, preferably between 0.5 and 0.001% by weight. For the treatment of seeds, quantities of active compound of generally 0.001 to 50 g, preferably 0.01 to 10 g, are employed per kg of seed. For the treatment of soil, active compound concentrations, at the point of action, of generally 0.00001 to 0.1% by weight, preferably of 0.0001 to 0.02%, are employed.

The present invention also provides a plant growth regulating or fungicidal composition containing as active ingredient a compound of the present invention in admixture with a solid or liquefied gaseous diluent or carrier or in admixture with a liquid diluent or carrier containing a surface-active agent. The present invention also provides a method of combating fungi which comprises applying to the fungi, or to a habitat thereof, a compound of the present invention alone or in the form of a composition containing as active ingredient a compound of the present invention in admixture with a diluent or carrier.

The present invention also provides a method of regulating the growth of plants which comprises applying to the plants, or to a habitat thereof, a compound of the present invention alone or in the form of a composition containing as active ingredient a compound of the present invention in admixture with a diluent or carrier.

The present invention further provides crops protected from damage by fungi by being grown in areas in which immediately prior to and/or during the time of the growing a compound of the present invention was applied alone or in admixture with a diluent or carrier.

The present invention further provides plants, the growth of which has been regulated by their being grown in areas in which immediately prior to and/or during the time of the growing a compound of the present invention was applied alone or in admixture with a diluent or carrier.

It will be seen that the usual methods of providing a harvested crop may be improved by the present invention.

PREPARATIVE EXAMPLES

Example 1

Preparation of the starting material (a)
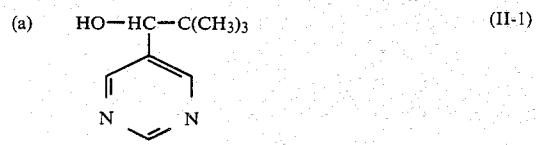
(II-1)

225 g of 5-bromopyrimidine were dissolved in 1.5 liters of absolute tetrahydrofuran/1,000 ml of absolute ether, and the solution was cooled to $-120°$ C. 250 ml of 50% strength n-butyl-lithium (in n-hexane) were added dropwise to the solution, during the course of 2 hours, at an internal temperature of $-105°$ to $-115°$ C. The mixture was further stirred for 1 hour at this temperature. 309 ml of trimethylacetaldehyde were then added dropwise during the course of 2 hours. The reaction mixture was then further stirred for 4 hours at this temperature. The reaction mixture was allowed to warm up to room temperature overnight, and 83 g of ammonium chloride, dissolved in a minimum quantity of water, were then added to it. The aqueous phase was separated off, and the organic phase was washed twice with saturated aqueous sodium chloride solution, dried over sodium sulphate and concentrated. 155 g (56% of theory) of 5-(1-hydroxy-2,2-dimethylpropyl)-pyrimidine of melting point 94°–96° C. were obtained after recrystallization of the residue from acetonitrile.

The following starting materials of the formula (II) were obtained by analogous methods:

TABLE 2

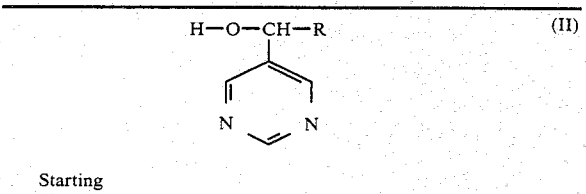
(II)

| Starting Material No. | R | Physical constants |
|---|---|---|
| II-2 | —CH(CH$_3$)$_2$ | boiling point: 80–82° C./0.02 mm Hg |
| II-3 |  | melting point: 85–87° C. |

TABLE 2-continued $$H-O-CH-R \quad (II)$$
(with pyrimidine ring)

| Starting Material No. | R | Physical constants |
|---|---|---|
| II-4 | -C₆H₄-Cl (4-Cl-phenyl) | |
| II-5 | $-(CH_2)_4CH_3$ | boiling point: 118–25° C./0.005 mbar |

(1)

(b) Cl—C₆H₄—CH₂—O—CH—C(CH₃)₃ (pyrimidinyl)

200 ml of 33% strength aqueous sodium hydroxide solution were added to a solution of 16.6 g of 5-(1-hydroxy-2,2-dimethylpropyl)-pyrimidine, 32.2 g of 4-chlorobenzyl chloride and 6 g of tetrabutylammonium bromide in 200 ml of toluene. The reaction mixture was stirred vigorously at room temperature for 18 hours.

The aqueous phase was separated off, and the toluene phase was diluted with toluene, washed four times with water and once with saturated aqueous sodium chloride solution, dried over sodium sulphate and concentrated. The oleaginous residue was dissolved in either/hexane, and the solution was treated with hydrogen chloride gas. The resulting crystalline precipitate was filtered off under suction and rinsed with ether, and ethyl acetate/1N sodium hydroxide solution was added to it, the free base again being formed.

20.3 g (70% of theory) of 5-[1-(4-chlorobenzyloxy)-2,2-dimethylpropyl]-pyrimidine of melting point 77°–78.5° C. were obtained after recrystallization from hexane.

Example 2

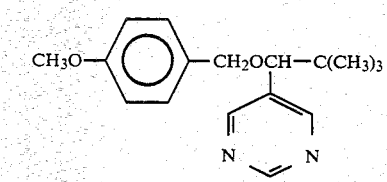

(2)

CH₃O—C₆H₄—CH₂OCH—C(CH₃)₃ (pyrimidinyl)

3.3 g of sodium hydride (80% strength in paraffin oil) were added to a solution of 16.6 g of 5-(1-hydroxy-2,2-dimethylpropyl)-pyrimidine in 150 ml of absolute dimethylsulphoxide, while stirring at room temperature. After 1 hour, a solution of 17.3 g of 4-methoxybenzyl chloride in 50 ml of absolute dimethylsulphoxide was added dropwise to the mixture. The reaction mixture was then further stirred for 3 days at room temperature.

The dimethylsulphoxide solution was concentrated, and the residue was taken up in ethyl acetate, washed once with water and once with saturated aqueous sodium chloride solution, dried over sodium sulphate and concentrated. The residue was dissolved in ether/hexane and the solution was treated with hydrogen chloride gas. The resulting crystalline precipitate was filtered off under suction and rinsed with ether, and ethyl acetate/1N sodium hydroxide solution was added to it, the free base being formed. 25.4 g (89% of theory) of 5-[1-(4-methoxybenzyloxy)-2,2-dimethylpropyl]-pyrimidine were obtained as a pale yellow oil with a refractive index $n_D^{20}$: 1.5388.

The following compounds of the general formula (I) were obtained in a corresponding manner:

TABLE 3

(I) X¹,X²,X³-phenyl—CH₂—O—CH—R (pyrimidinyl)

| Compound No. | $X^1$ | $X^2$ | $X^3$ | R | Melting point (°C.) or refractive index ($n_D^{20}$) |
|---|---|---|---|---|---|
| 3 | 2-Cl | 6-F | H | $-C(CH_3)_3$ | 63–64 |
| 4 | 4-CH₃ | H | H | $-C(CH_3)_3$ | 39–44 |
| 5 | 4-F | H | H | $-C(CH_3)_3$ | 1,5230 |
| 6 | 2-Cl | 4-Cl | H | $-C(CH_3)_3$ | 59–61 |
| 7 | 3-Cl | 4-Cl | H | $-C(CH_3)_3$ | 63–66 |
| 8 | 4-phenyl | | H | $-C(CH_3)_3$ | 95–97 |
| 9 | 4-Cl | H | H | $-CH(CH_3)_2$ | 1.5478 |
| 10 | 4-F | H | H | $-CH(CH_3)_2$ | 1.5242 |
| 11 | 4-CF₃ | H | H | $-C(CH_3)_3$ | 1.4986 |
| 12 | 4-OCF₃ | H | H | $-C(CH_3)_3$ | 1.4949 |
| 13 | 4-OCH₃ | H | H | cyclohexyl | 1.5511 |
| 14 | 4-Cl | H | H | cyclohexyl | 1.5602 |
| 15 | 4-F | H | H | cyclohexyl | 1.5391 |
| 16 | 3-Cl | 4-Cl | H | cyclohexyl | 1.5622 |
| 17 | 2-Cl | 4-Cl | H | cyclohexyl | 1.5687 |
| 18 | H | H | H | $-C(CH_3)_3$ | 1.5345 |
| 19 | 4-Cl | H | H | $-C(CH_3)_3$ | 140–142 (×HCl) |
| 20 | 4-OCH₃ | H | H | $-(CH_2)_4CH_3$ | 1.5320 |
| 21 | 4-Cl | H | H | $-(CH_2)_4CH_3$ | 1.5348 |
| 22 | 2-Cl | 4-Cl | H | $-(CH_2)_4CH_3$ | 1.5459 |
| 23 | 3-Cl | 4-Cl | H | $-(CH_2)_4CH_3$ | 1.5402 |
| 24 | 4-F | H | H | $-(CH_2)_4CH_3$ | 1.5155 |
| 25 | 2-Cl | 4-Cl | H | $-CH(CH_3)_2$ | 1.5592 |

USE EXAMPLES

The plant-growth regulating and fungicidal activity of the compounds of this invention is illustrated by the following examples wherein the compounds according to the present invention are each identified by the number (given in brackets) from the preparative examples and Table 3 hereinabove.

The known comparison compounds are identified as follows:

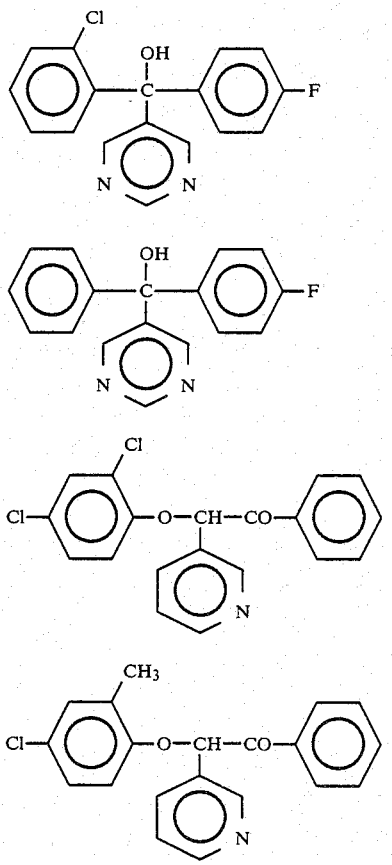

Example 3

Inhibition of growth of grass (Festuca pratensis)

Solvent: 30 parts by weight of dimethylformamide
Emulsifier: 1 part by weight of polyoxyethylene sorbitan monolaurate To produce a suitable preparation of active compound, 1 part by weight of active compound was mixed with the stated amounts of solvent and emulsifier and the mixture was made up to the desired concentration with water.

Grass (*Festuca pratensis*) was grown in a greenhouse up to a height in growth of 5 cm. In this stage, the plants were sprayed with the preparations of active compound until dripping wet. After 3 weeks, the additional growth was measured and the inhibition of growth in percent of the additional growth of the control plants was calculated. 100% inhibition of growth meant that growth had stopped and 0% denoted a growth corresponding to that of the control plants.

In this test, the compounds (1), (5), (6), (7) (9) and (10) showed a better inhibition of growth than the compounds (A) and (B) known from the state of the art.

Example 4

Inhibition of growth of barley

Solvent: 30 parts by weight of dimethylformamide
Emulsifier: 1 part by weight of polyoxyethylene sorbitan monolaurate To produce a suitable preparation of active compound, 1 part by weight of active compound was mixed with the stated amounts of solvent and emulsifier and the mixture was made up to the desired concentration with water.

Barley plants were grown in a greenhouse to the 2-leaf stage. In this stage, the plants were sprayed with the preparations of active compound until dripping wet. After 3 weeks, the additional growth was measured on all of the plants and the inhibition of growth in percent of the additional growth of the control plants was calculated. 100% inhibition of growth meant that growth had stopped and 0% denoted a growth corresponding to that of the control plants.

In this test, the compounds (6), (18), (9) and (10) showed a better inhibition of growth than the compounds (A) and (B) known from the state of the art.

Example 5

Inhibition of growth of cotton

Solvent: 30 parts by weight of dimethylformamide
Emulsifier: 1 part by weight of polyoxyethylene sorbitan monolaurate To produce a suitable preparation of active compound, 1 part by weight of active compound was mixed with the stated amounts of solvent and emulsifier and the mixture was made up to the desired concentration with water.

Cotton plants were grown in a greenhouse until the 5th secondary leaf had unfolded completely. In this stage, the plants were sprayed with the preparations of active compound until dripping wet. After 3 weeks, the additional growth in percent of the additional growth of the control plants was calculated. 100% inhibition of growth means that growth had stopped and 0% denoted a growth corresponding to that of the control plants.

In this test, the compound (1), (3), (5), (6), (7), (8), (14), (15), (17), (9) and (10) showed a better inhibition of growth than the compound (A) known from the state of the art.

Example 6

Inhibition of growth of soy beans

Solvent: 10 parts by weight of methanol
Emulsifier: 2 parts by weight of polyoxyethylene sorbitan monolaurate To produce a suitable preparation of active compound, 1 part by weight of active compound was mixed with the stated amounts of solvent and emulsifier and the mixture was made up to the desired concentration with water.

Young soy bean plants, in the stage at which the first secondary leaves had unfolded, were sprayed with the preparations of active compound until dripping wet. After 2 weeks, the additional growth was measured and the inhibition of growth in % of the additional growth of the control plants was calculated. 100% meant that growth had stopped and 0% denoted a growth corresponding to that of the control plants.

In this test, the compounds (1), (3), (4), (5), (6), (7), (14), (12), (11), (17), (18), (9), (10) and (2) showed a better inhibition of growth than the compound (A) known from the state of the art.

Example 7

Inhibition of growth of sugar beet

Solvent: 30 parts by weight of dimethylformamide
Emulsifier: 1 part by weight of polyoxyethylene sorbitan monolaurate To produce a suitable preparation of active compound, 1 part by weight of active compound was mixed with the stated amounts of solvent and emulsifier and the mixture was made up to the desired concentration with water.

Sugar beet was grown in a greenhouse until formation of the cotyledons was complete. In this stage, the plants were sprayed with the preparation of active compound until dripping wet. After 14 days, the additional growth of the plants was measured and the inhibition of growth in percent of the additional growth of the control plants was calculated. 0% inhibition of growth denoted a growth which corresponded to that of the control plants. 100% inhibition of growth meant that growth had stopped.

In this test, the compounds (1), (3), (4), (5), (6), (7), (14), (12), (11), (17), (13), (18), (9), (10), (2) and (8) showed a better inhibition of growth than the compounds (A) and (B) known from the state of the art.

Example 8

Erysiphe test (barley)/protective/

Solvent: 100 parts by weight of dimethylformamide
Emulsifier: 0.25 part by weight of alkyl aryl polyglycol ether To produce a suitable preparation of active compound, 1 part by weight of active compound was mixed with the stated amounts of solvent and emulsifier, and the concentrate was diluted with water to the desired concentration.

To test for protective activity, young plants were sprayed with the preparation of active compound until dew-moist. After the spray coating had dried on, the plants were dusted with spores of *Erysiphe graminis* f. sp. hordei.

The plants were placed in a greenhouse at a temperature of about 20° C. and a relative atmospheric humidity of about 80%, in order to promote the development of powdery mildew pustules.

Evaluation was carried out 7 days after the inoculation.

In this test, a significant superiority in activity, compared with the compounds (C) and (D) known from the state of the art, was shown, for example, by the compounds (1), (3), (4), (5), (6), (7) and (8).

Example 9

Increase of the photosynthesis in soy beans

It has been found that the compounds (14) and (16) cause a significant increase of photosynthesis in soy beans.

It will be appreciated that the instant specification and examples are set forth by way of illustration and not limitation, and that various modifications and changes may be made without departing from the spirit and scope of the present invention.

We claim:

1. A fungicidal or plant-growth stunting composition comprising a plant compatible diluent in admixture with a fungicidally or plant-growth-stunting effective amount of a benzyl-pyrimidinylalkyl-ether of the formula

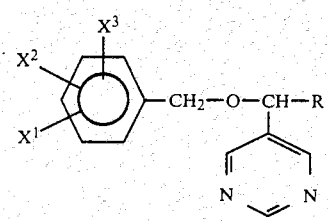

in which
R is alkyl having 1 to 8 carbon atoms; cycloalkyl which has 3 to 7 carbon atoms and which is optionally substituted by alkyl having 1 to 4 carbon atoms; or phenyl which is optionally substituted by halogen, alkyl having 1 to 4 carbon atoms, alkoxy having 1 to 4 carbon atoms and/or halogenoalkyl having 1 or 2 carbon atoms and 1 to 5 halogen atoms,
$X^1$ is hydrogen, halogen, alkyl having 1 to 4 carbon atoms, cycloalkyl having 3 to 7 carbon atoms, alkoxy having 1 to 4 carbon atoms, alkylthio having 1 to 4 carbon atoms, halogenoalkyl having 1 to 4 carbon atoms and 1 to 5 halogen atoms, halogenoalkoxy having 1 to 4 carbon atoms and 1 to 5 halogen atoms, halogenoalkylthio having 1 to 4 carbon atoms and 1 to 5 halogen atoms, phenyl which is optionally substituted by halogen and/or by alkyl having 1 to 4 carbon atoms, phenoxy which is optionally substituted by halogen and/or by alkyl having 1 to 4 carbon atoms, phenylalkyl which has 1 to 4 carbon atoms in the alkyl part and which is optionally substituted in the phenyl part by halogen and/or by alkyl having 1 to 4 carbon atoms, or phenylalkoxy which has 1 to 4 carbon atoms in the alkoxy part and which is optionally substituted in the phenyl part by halogen and/or by alkyl having 1 to 4 carbon atoms, and
$X^2$ and $X^3$ each independently is hydrogen, halogen, alkyl having 1 to 4 carbon atoms, cycloalkyl having 3 to 7 carbon atoms, alkoxy having 1 to 4 carbon atoms, alkylthio having 1 to 4 carbon atoms or halogenoalkyl, halogenoalkoxy or halogenoalkylthio each having 1 to 4 carbon atoms and 1 to 5 halogen atoms,
or an acid addition salt or metal salt complex thereof.

2. A composition according to claim 1, in which
R is alkyl with 1 to 8 carbon atoms, cycloalkyl with 3 to 7 carbon atoms or phenyl,
$X^1$ is hydrogen, halogen, alkyl with 1 to 4 carbon atoms, alkoxy with 1 to 4 carbon atoms, halogenoalkyl with 1 to 4 carbon atoms and 1 to 5 halogen atoms, halogenoalkoxy with 1 to 4 carbon atoms and 1 to 5 halogen atoms or phenyl,
$X^2$ is hydrogen or halogen, and
$X^3$ is hydrogen
or a hydrochloric acid addition salt thereof.

3. A method of stunting the growth of plants, comprising applying to the plants, or to a habitat thereof, a plant-growth-stunting effective amount of a benzyl-pyrimidinylalkyl-ether of the formula

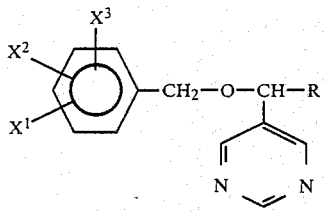

in which

R is alkyl, optionally substituted cycloalkyl or optionally substituted phenyl, and $X^1$, $X_2$ and $X^3$ each independently is hydrogen, halogen, alkyl, cycloalkyl, alkoxy, alkylthio, halogenoalkyl, halogenoalkoxy, halogenoalkylthio, cyano, optionally substituted phenoxy, optionally substituted phenylalkyl or optionally substituted phenylalkoxy, or an acid addition salt or metal salt complex thereof.

4. The method according to claim 3, wherein such compound is

5-[1-(4-chlorobenzyloxy)-2,2-dimethylpropyl]-pyrimidine,

5-[1-(4-methoxybenzyloxy)-2,2-dimethylpropyl]-pyrimidine,

5-[1-(2-chloro-6-fluorobenzyloxy)-2,2-dimethylpropyl]-pyrimidine,

5-[1-(4-fluorobenzyloxy)-2,2-dimethylpropyl]-pyrimidine or

5-[1-(2,4-dichlorobenzyloxy)-2,2-dimethylpropyl]-pyrimidine, or an acid addition salt or metal salt complex thereof.

5. A composition according to claim 1, in which

R is isopropyl, isobutyl, tert.-butyl, n-pentyl, n-hexyl, optionally methyl-substituted cyclopentyl or cyclohexyl, or phenyl which is optionally substituted by fluorine, chlorine, methyl, methoxy or trifluoromethyl, $X^1$ is hydrogen, fluorine, chlorine, methyl, tert.-butyl, cyclohexyl, methoxy, methylthio, trifluoromethyl, trifluoromethoxy, trifluoromethylthio, cyano, or phenyl, phenoxy, benzyl or benzyloxy, each of which is optionally substituted by fluorine, chlorine or methyl, $X^2$ is hydrogen, fluorine, chlorine, methyl, tert.-butyl, cyclohexyl, methoxy, methylthio, trifluoromethyl, trifluoromethoxy or trifluoromethylthio, and $X^3$ is hydrogen, fluorine, chlorine, methyl, methoxy, methyl or trifluoromethyl, or an addition salt thereof with a hydrohalic acid, phosphoric acid, nitric acid, sulphuric acid, a sulphonic acid or a monofunctional or bifunctional carboxylic or hydroxycarboxylic acid, or a complex thereof with a salt, the metal of the salt being copper, zinc, manganese, magnesium, tin, iron or nickel and the anion of the salt being halide, phosphate or sulphate.

* * * * *

UNITED STATES PATENT AND TRADEMARK OFFICE
CERTIFICATE OF CORRECTION

PATENT NO. : 4,515,617
DATED     : May 7, 1985
INVENTOR(S) : Graham Holmwood, et al.

It is certified that error appears in the above-identified patent and that said Letters Patent is hereby corrected as shown below:

| | |
|---|---|
| Col. 6, line 22 | After "percent" insert -- . -- |
| Col. 9, line 47 | Before "frost" delete "of" (2nd occurrence) and substitute --to-- |
| Col. 9, lines 66-68 | Underline "Plasmodiophoromycetes", "Oomycetes", "Chytridiomycetes", "Zygomycetes", "Ascomycetes", "Basidiomycetes", and "Deuteromycetes" |
| Col. 19, line 15 | Delete "$X_2$" and substitute --$x^2$-- |

Signed and Sealed this

Twenty-ninth Day of October 1985

[SEAL]

Attest:

DONALD J. QUIGG

Attesting Officer

Commissioner of Patents and
Trademarks—Designate